United States Patent [19]

Schnettler et al.

[11] Patent Number: 4,698,353

[45] Date of Patent: Oct. 6, 1987

[54] CARDIOTONIC HETEROCYCLIC OXAZOLONES

[75] Inventors: Richard A. Schnettler; Winton D. Jones, Jr.; George P. Claxton, all of Cincinnati, Ohio

[73] Assignee: Merrell Dow Pharmaceuticals Inc., Cincinnati, Ohio

[21] Appl. No.: 797,580

[22] Filed: Nov. 13, 1985

[51] Int. Cl.$^4$ .................. C07D 401/00; C07D 419/00; C07D 413/00; C07D 263/04
[52] U.S. Cl. .................................... 514/340; 546/275; 546/278; 548/232; 514/341; 514/376
[58] Field of Search ................ 546/275, 278; 548/232; 514/340, 341, 376

[56] References Cited

U.S. PATENT DOCUMENTS

| | | | |
|---|---|---|---|
| 3,879,410 | 4/1975 | Bottari et al. | 548/232 |
| 4,188,323 | 2/1980 | Pestellini et al. | 548/232 |
| 4,532,250 | 7/1985 | Stout et al. | 548/232 |

FOREIGN PATENT DOCUMENTS

| | | | |
|---|---|---|---|
| 2935902 | 4/1981 | Fed. Rep. of Germany | 546/275 |
| 7654553 | 11/1974 | Japan | 548/232 |
| 7611763 | 1/1976 | Japan | 548/232 |
| 1305273 | 1/1973 | United Kingdom | 548/232 |
| 427015 | 12/1974 | U.S.S.R. | 548/232 |

OTHER PUBLICATIONS

Chemical Abstracts, vol. 86(5) abstract no. 29695s, Jan. 31, 1977 abstracting B. Krieg and P. Konieczny, Justus Liebigs Ann. Chem., 10, 1862–72 (1976).
Nakagawa M., et al., Agric. Biol. Chem. 38(11):2205–8 (1974).
Nakagawa M. et al., Agric. Biol. Chem. 39(9):1763–73 (1975).
Fukumi H. et al., Heterocycles 12(10):1297–9 (1979).
Shvaika O. P., Klimisha G. P. Dopov. Akad. Nauk Ukr. RSR, Ser. B 32(4):350–2 (1970).
Bottari F., et al., J. Med Chem. 15(1):39–42 (1972).
Roderhorst R. M., Koch T. H., J. Am. Chem. Soc. 97(25):7298–304 (1975).
Saettorne M. F., et al., Gazz. Chim. Ital. 96(11):1615–29 (1966).
Krieg B., Konieczny P. Justus Liebigs Ann. Chem. (10:1862–70 (1976).
Dziomko V. A., Ivashchenko A. V., ZH. Org, Khim. 9(10):2191–4 (1973).

*Primary Examiner*—John M. Ford
*Assistant Examiner*—Robert C. Whittenbaug
*Attorney, Agent, or Firm*—Stephen L. Nesbitt

[57] ABSTRACT

Heterocyclic oxazolones enhance myocardial contractile force and cardiac function and are used as cardiotonics in the treatment of heart failure.

21 Claims, No Drawings

CARDIOTONIC HETEROCYCLIC OXAZOLONES

BACKGROUND OF THE INVENTION

This invention relates to certain heterocyclic oxazolones and their use as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea and pulmonary edema.

Treatment involves either removal or correction of the underlying cause or involves control of the heart failure state. Management or control can be accomplished by increasing cardiac output or by decreasing cardiac workload. While workload can be reduced by reduction of physical activities and physical and emotional rest, increasing cardiac output has traditionally involved therapy with digitalis or a digitalis glycoside and more recently vasodilator therapy. Digitalis stimulates contractile force of the heart which increases cardiac output and improves ventricular emptying. In this way digitalis therapy normalizes venous pressure and reduces peripheral vasoconstriction, circulatory congestion and organ hypoperfusion.

Unfortunately optimal doses of digitalis vary with the patient's age, size and condition and the therapeutic to toxic ratio is quite narrow. In most patients the lethal dose is only about five to ten times the minimal effective dose with toxic effects becoming apparent at only 1.5 to 2.0 times the effective dose. For these reasons, dose must be carefully tailored to suit the individual and frequent clinical examination and electrocardiogram are necessary to detect early signs of digitalis intoxication. Despite this care digitalis intoxication is reported in up to one-fifth of hospitalized patients undergoing therapy.

Vasodilator therapy increases cardiac output and improves ventricular emptying by reducing the systemic blood pressure against which the heart must pump. However, in severe heart failure as vasodilator alone may not improve cardiac function sufficiently due to the weakness of the myocardial contractility necessitating the concomitant use of digitalis. Moreover a rapid tolerance has been reported to develop the effects of vasodilator therapy in heart failure patients. The need for less toxic and more effective cardiotonic agents is readily apparent. Applicants have discovered certain heterocyclic oxazolones which possess potent cardiotonic activity and by comparison to digitalis have few toxic effects.

SUMMARY OF THE INVENTION

This invention is directed to heterocyclic oxazolones of formula 1

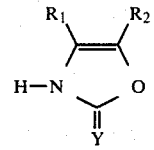

wherein
Y is an oxygen or sulfur group;
$R_1$ is a hydrogen or a $(C_1-C_5)$ alkyl group when $R_2$ is R;
$R_2$ is a hydrogen or a $(C_1-C_5)$ alkyl group when $R_1$ is R; and
R is a 2-, 3-, or 4-pyridyl group optionally sustituted with a hydroxy, halogen, $(C_1-C_5)$alkyl, $(C_1-C_5)$alkoxy, $(C_1-C_5)$ alkylthio, $(C_1-C_5)$alkylsulfinyl, $(C_1-C_5)$alkylsulfonyl, cyano, carboxy, carb$(C_1-C_5)$alkoxy, carbamido, $(C_1-C_5)$alkanoylamino or imidazolyl group, or R is a 2- or 3-furanyl, 2- or 3-thienyl or 2- or 3-pyranyl group.

DETAILED DESCRIPTION OF THE INVENTION

The formula 1 compounds exist in several tautomeric forms. Throughout this disclosure, heterocyclic oxazolones of formula 1 are intended to include these tautomers as well.

The ring nitrogen of the formula 1 compounds can be substituted with a $(C_1-C_5)$ alkyl group, an alkanoyl group such as an acetyl group, or a benzoyl group. These nitrogen substituted compounds are equivalent to the unsubstituted compounds primarily because the substituent is cleaved upon administration to a patient but also because many of the nitrogen substituted compounds independently possess significant ability to enhance myocardial contractile force and are useful cardiotonic agents.

As used herein the term $(C_1-C_5)$ alkyl and the alkyl portion of the alkoxy, alkylthio, alkylsulfinyl, alkylsulfonyl, carbalkoxy, and alkanoylamino groups means a straight or branched alkyl group of from one to five carbon atoms. Illustrative examples of a $(C_1-C_5)$ alkyl group are methyl, ethyl, isopropyl, butyl, sec-butyl and pentyl. The term halogen means a fluoro, chloro, bromo or iodo group. Imidazolyl means 1-, 2-, 3-, 4- or 5-imidazolyl.

As is true for most classes of therapeutically effective compounds, certain subclasses are more effective than others. In this instance those compounds of formula 1 wherein Y is an oxo group are preferred. Also preferred are those compounds wherein $R_1$ is a $(C_1-C_5)$ alkyl group or wherein $R_2$ is a $(C_1-C_5)$ alkyl group. More preferred are those compounds of formula 1 wherein $R_1$ is a $(C_1-C_5)$ alkyl group and $R_1$ is an optionally substituted pyridyl group. The most preferred compounds of formula 1 are those wherein $R_1$ is a methyl, ethyl or propyl group and wherein $R_2$ is an unsubstituted pyridyl group.

The compounds of formula 1 can be prepared by standard techniques analagously known in the art. In fact many of the formula 1 compounds are reported in the chemical literature. For example those compounds of formula 1 wherein $R_1$ is an optionally substituted phenyl group and $R_2$ is a hydrogen group can be prepared by the procedures described in U.S. Pat. No. 3,879,410. In another procedure a compound of formula 2A or 2B

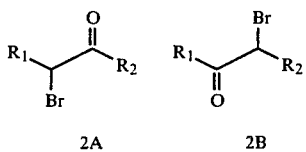

wherein $R_1$ and $R_2$ are as defined above is allowed to react with a cyanate or thiocyanate salt to form the corresponding isocyanate or isothiocyanate of formula 3A or 3B

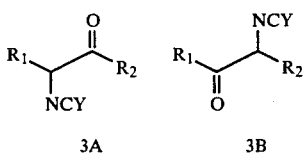

wherein Y, $R_1$ and $R_2$ are as defined above. The isocyanate compound when heated, typically as a melt at from 90° to 110° C. without solvent condenses to form a compound of formula 1.

Another procedure involves cyclizing a hydroxyketone of structure 4A or 4B

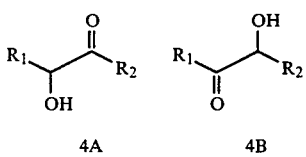

wherein $R_1$ and $R_2$ are as defined above by reaction with a cyanate or thiocyanate salt in the presence of an acid.

The bromo-ketones of formula 2A or 2B are either known in the art or can be readily prepared by standard techniques. For example the des-bromo analog of a structure 2A or 2B compound can be treated with bromine. Where the group adjacent to the carbon to be brominated is a hydrogen or a $(C_1-C_5)$ alkyl group, a radical initiator can be used to promote the bromination. Suitable initiators include iron metal and N-bromosuccinimide. The bromination an also be accomplished the addition of centrated hydrobromic acid, typically 48% aqueous hydrobromic acid, to a solution containing des-bromo compound. The structure 4A and 4B hydroxyketones can also be readily prepared in any suitable manner. For example a structure 2A or 2B bromo-ketone can be allowed to react with an acetate salt, preferaly potassium acetate, to form the corresponding acetyloxyketone which upon treatment with an acid, such as hydrochloric acid, yields the desired structure 4A or 4B compound.

The compounds of formula 1 are cardiotonic agents useful in the treatment of heart failure. The utility of formula 1 compounds as cardiotonics may be determined by administering the test compound (0.1-100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left heart to record left atrial pressure or left ventricular pressure. Heart failure is induced by administering sodium pentobarbital (20 to 40 mg/kg) followed by a continuous infusion of 0.25-2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severly depressed. Reversal of these effects by the test compound indicates cardiotonic activity.

The compounds may be administered in various manners to achieve the desired effect. The compounds may be administered alone or in the form of pharmaceutical preparations to the patient being treated either topically, orally or parenterally, that is, intravenously or intramuscularly. The amount of compound administered will vary with the patient, the severity of the cardiac failure and the mode of administration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferaly about 15 to 500 mg of the active ingredient. For parenteral administration a unit dosage may contain, for example, from 5 to 700 mg of the active ingredient, preferably about 15 to 210 mg. Repetitive daily administration of the compounds may be desired and will vary with the condition of the patient and the mode of administration.

As used herein, the term "patient" is taken to mean warm blooded animals, for example, birds, such as chickens, and turkeys, and mammals, such as sheep, horses, bovine cows and bulls, pigs, dogs, cats, rats, mice and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

The following specific examples further illustrate the preparation and use of the compounds of formula 1 but are not intended to limit the scope of the invention.

EXAMPLE 1

4-Ethyl-5-Pyridin-4-yl-2(3H)-Oxazolone

1-Hydroxy-1-(4-pyridyl)butan-2-one (26.4 g, 0.16 mol) was dissolved in 350 ml of 2N HCl. Potassium cyanate (38.9 g, 0.48 mol) was added portionwise to this solution over a period of one hour with stirring. After the addition was complete, concentrated hydrochloric acid was added until the pH of the solution was one. After an additional hour the reaction mixture was made basic by addition of sodium bicarbonate solution and the resulting mixture was stirred overnight. The resulting solid precipitated was collected and recrystallized twice from 50% aqueous ethanol to yield the title compound (14.4 g, 47% of theoretical yield), m.p. 287°–289° C. (dec.).

Using the procedure above but using 1-(hydroxy)-1-(4-pyridyl)pentan-2-one or 1-(hydroxy)-1-(4-pyridyl)-propan-2-one instead of 1-hydroxy-1-(4-pyridyl)butan-2-one results in 4-propyl-5-pyridin-4-yl-2(3H)-oxazolone, m.p. 257°–259° C. (dec.) or 4-methyl-5-pyridin-4-yl-2(3H)-oxazolone, m.p. >310° C.

EXAMPLE 2

5-Ethyl-4-(2-pyridyl)-2(3H)-oxazolone

Potassium cyanate (35.4 g, 0.44 mol) was added to a solution of 2-hydroxy-1-(2-pyridyl)butan-1-one (31 g, 0.15 mol) in 250 ml of 2N HCl diluted with 300 ml of water. After 1 hour the acidity was adjusted (pH=1) with concentrated hydrochloric acid and then allowed to stir overnight. The mixture was made basic by addition of aqueous sodium bicarbonate. The resulting gummy precipitate was chromatographed on silica gel and recrystallized twice from 50% aqueous ethanol to give the title compound, m.p 196°–97° C. (dec.).

EXAMPLE 3

A tablet is prepared from

| | |
|---|---|
| 4-propyl-5-pyridin-4-yl-2(3H)—oxazolone | 250 mg |
| starch | 40 mg |
| talc | 10 mg |
| magnesium stearate | 10 mg |

EXAMPLE 4

A capsule is prepared from

| | |
|---|---|
| 4-ethyl-5-pyridin-4-yl-2(3H)oxazolone | 400 mg |
| talc | 40 mg |
| sodium carboxymethylcellulose | 40 mg |
| starch | 120 mg |

What we claim is:

1. A heterocyclic oxazolone of the formula $$\begin{array}{c} R_1 \diagdown \quad \diagup R_2 \\ \diagup = \diagdown \\ H-N \quad \quad O \\ \diagdown \diagup \\ \| \\ Y \end{array}$$

wherein
Y is an oxygen or sulfur group;
$R_1$ is a hydrogen or a ($C_1$–$C_5$) alkyl group when $R_2$ is R;
$R_2$ is a hydrogen or a ($C_1$–$C_5$) alkyl group when $R_1$ is R; and
R is a 2-, 3- or 4-pyridyl group optionally substituted with a hydroxy, halogen, ($C_1$–$C_5$) alkyl, ($C_1$–$C_5$) alkoxy, ($C_1$–$C_5$) alkylthio, ($C_1$–$C_5$)alkylsulfinyl, ($C_1$–$C_5$)alkylsulfonyl, cyano, carboxy, carb($C_1$–$C_5$)alkoxy, carbamido, ($C_1$–$C_5$)alkanoylamino, or imidazolyl group, or R is a 2- or 3-furanyl, 2- or 3-thienyl or 2- or 3-pyranyl group with the proviso that when either of $R_1$ or $R_2$ is a hydrogen, R cannot be a 2- or 3-thienyl group.

2. A heterocyclic oxazolone of claim 1 wherein Y is an oxygen group.

3. A heterocyclic oxazolone of claim 2 wherein $R_1$ or $R_2$ is a ($C_1$–$C_5$) alkyl group.

4. A heterocyclic oxazolone of claim 2 wherein R is an optionally substituted 2-, 3- or 4-pyridyl group.

5. A heterocyclic oxazolone of claim 2 wherein $R_1$ is a methyl, ethyl or propyl group.

6. A heterocyclic oxazolone of claim 2 wherein $R_2$ is an unsubstituted pyridyl group.

7. A heterocyclic oxazolone of claim 6 wherein $R_1$ is a methyl, ethyl or propyl group.

8. A method of treating heart failure in a patient in need thereof which comprises administering to the patient a cardiotonically effective amount of a heterocyclic oxazolone of the formula $$\begin{array}{c} R_1 \diagdown \quad \diagup R_2 \\ \diagup = \diagdown \\ H-N \quad \quad O \\ \diagdown \diagup \\ \| \\ Y \end{array}$$

wherein
Y is an oxygen or sulfur group;
$R_1$ is a hydrogen or a ($C_1$–$C_5$) alkyl group when $R_2$ is R;
$R_2$ is a hydrogen or a ($C_1$–$C_5$) alkyl group when $R_1$ is R; and
R is a 2-, 3- or 4-pyridyl group optionally substituted with a hydroxy, halogen, ($C_1$–$C_5$) alkyl, ($C_1$–$C_5$) alkoxy, ($C_1$–$C_5$) alkylthio, ($C_1$–$C_5$)alkylsulfinyl, ($C_1$–$C_5$)alkylsulfonyl, cyano, carboxy, carb($C_1$–$C_5$)alkoxy, carbamido, ($C_1$–$C_5$)alkanoylamino, or imidazolyl group, or R is a 2- or 3-furanyl, 2- or 3-thienyl or 2- or 3-pyranyl group.

9. A method of claim 8 wherein Y is an oxygen group.

10. A method of claim 9 wherein $R_1$ or $R_2$ is a ($C_1$–$C_5$) alkyl group.

11. A method of claim 9 wherein R is an optionally substituted 2-, 3- or 4-pyridyl group.

12. A method of claim 9 wherein $R_1$ is a methyl, ethyl or propyl group.

13. A method of claim 9 wherein $R_2$ is an unsubstituted pyridyl group.

14. A method of claim 13 wherein $R_1$ is a methyl, ethyl or propyl group.

15. A method of enhancing myocardial contractile force in a patient in need thereof which comprises administering to the patient an effective amount of an heterocyclic oxazolone of the formula

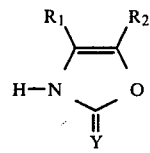

wherein
Y is an oxygen or sulfur group;
$R_1$ is a hydrogen or a ($C_1$–$C_5$) alkyl group when $R_2$ is R;
$R_2$ is a hydrogen or a ($C_1$–$C_5$) alkyl group when $R_1$ is R; and
R is a 2-, 3- or 4-pyridyl group optionally substituted with a hydroxy, halogen, ($C_1$–$C_5$) alkyl, ($C_1$–$C_5$) alkoxy, ($C_1$–$C_5$) alkylthio, ($C_1$–$C_5$)alkylsulfinyl, ($C_1$–$C_5$)alkylsulfonyl, cyano, carboxy, carb($C_1$–$C_5$)alkoxy, carbamido, ($C_1$–$C_5$)alkanoylamino, or imidazolyl group, or R is a 2- or 3-furanyl, 2- or 3-thienyl or 2- or 3-pyranyl group.

16. A method of claim 15 wherein Y is an oxygen group.

17. A heterocyclic oxazolone of claim 16 wherein $R_1$ or $R_2$ is a ($C_1$–$C_5$) alkyl group.

18. A method of claim 16 wherein R is an optionally substituted 2-, 3- or 4-pyridyl group.

19. A method of claim 16 wherein $R_1$ is a methyl, ethyl or propyl group.

20. A method of claim 16 wherein $R_2$ is an unsubstituted pyridyl group.

21. A method of claim 20 wherein $R_1$ is a methyl, ethyl or propyl group.

* * * * *